US00PP11394P

United States Patent [19]

Trees

[11] Patent Number: Plant 11,394

[45] Date of Patent: May 30, 2000

[54] GERANIUM PLANT NAMED 'BFP-1561'

[75] Inventor: Scott C. Trees, Nipomo, Calif.

[73] Assignee: Ball FloraPlant, a division of Ball Horticultural Co., West Chicago, Ill.

[21] Appl. No.: 09/114,124

[22] Filed: Jul. 13, 1998

[51] Int. Cl.[7] ..... A01H 5/00

[52] U.S. Cl. ..... Plt./325

[58] Field of Search ..... Plt./325, 328

*Primary Examiner*—Howard J. Locker
*Assistant Examiner*—Kent L. Bell
*Attorney, Agent, or Firm*—C. A. Whealy

[57] ABSTRACT

A new and distinct cultivar of Geranium plant named 'BFP-1561', characterized by its numerous single white and purple bi-colored flowers; upright and rounded growth habit; basal branching; and dark green leaves with a distinct zonation pattern.

1 Drawing Sheet

BACKGROUND OF THE INVENTION

The present invention relates to a new and distinct cultivar of Geranium plant, botanically known as *Pelargonium*× *hortorum,* and hereinafter referred to by the cultivar name 'BFP-1561'.

The new Geranium is a product of a planned breeding program conducted by the Inventor in Arroyo Grande, Calif. The objective of the breeding program was to develop new cultivars with excellent basal branching, medium growth habit, numerous flowers and umbels, and interesting flower and foliage colors.

The new Geranium originated from a self-pollination made by the Inventor of the proprietary *Pelargonium*× *hortorum* selection 4077-1. The cultivar 'BFP-1561' was discovered and selected by the Inventor as a flowering plant within the progeny of the stated cross in a controlled environment in Arroyo Grande, Calif., on Sep. 15, 1996.

Asexual reproduction of the new cultivar by terminal cuttings taken at Arroyo Grande, Calif., has shown that the unique features of this new Geranium are stable and reproduced true to type in successive generations of asexual reproduction.

SUMMARY OF THE INVENTION

The following traits have been repeatedly observed and are determined to be the unique characteristics of 'BFP-1561'. These characteristics in combination distinguish 'BFP-1561' as a new and distinct cultivar:

1. Numerous single white and purple bi-colored flowers.
2. Upright and rounded growth habit.
3. Basal branching.
4. Dark green leaves with a distinct zonation pattern.

The new Geranium can be compared to the cultivar, 'Starburst Red' (disclosed in U.S. Plant Pat. No. 9,229). However, in side-by-side comparisons conducted by the Inventor in Arroyo Grande, Calif., plants of the new Geranium differ from plants of the cultivar 'Starburst Red' in the following characteristics:

1. Plants of the new Geranium are more compact and less vigorous than plants of the cultivar 'Starburst Red'.

2. Leaves of the new Geranium are lighter green than leaves of plants of the cultivar 'Starburst Red'.

3. Flower color of plants of the new Geranium is white and purple bi-colored whereas flower color of plants of the cultivar 'Starburst Red' is red and white bi-colored.

4. Plants of the new Geranium have shorter peduncles than plants of the cultivar 'Starburst Red'.

A detailed comparison of plants of the cultivar 'BFP-1561' and the cultivar 'Starburst Red' appears in Chart A at the end of the specification.

BRIEF DESCRIPTION OF THE PHOTOGRAPH

The accompanying colored photograph illustrates the overall appearance of the new cultivar, showing the colors as true as it is reasonably possible to obtain in colored reproduction of this type. The photograph comprises a side perspective view of a typical plant of 'BFP-1561'. Flower and foliage colors in the photograph may appear different from the actual colors due to light reflectance.

DETAILED BOTANICAL DESCRIPTION

The cultivar 'BFP-1561' has not been observed under all possible environmental conditions. The phenotype may vary somewhat with variations in environment such as temperature and light intensity, without, however, any variance in genotype. The following observations, measurements and comparisons describe plants grown in 10-cm pots in Arroyo Grande, Calif., under commercial practice in a glass-covered greenhouse with day temperatures about 22° C. and night temperatures about 18° C.

In the following description, color references are made to The Royal Horticultural Society Colour Chart except where general terms of ordinary dictionary significance are used.

Botanical classification: *Pelargonium*×*hortorum* cultivar 'BFP-1561'.

Parentage:

*Male parent.*—Proprietary *Pelargonium*×*hortorum* selection 4077-1.

*Female parent.*—Proprietary *Pelargonium*×*hortorum* selection 4077-1.

Propagation:

*Type cutting.*—Terminal cuttings.

*Time to initiate roots.*—About 7 days with 18° C.

*Time to develop roots.*—About 21 days with 18° C.

*Rooting habit.*—Fibrous and freely branching.

Plant description:

*General appearance.*—Upright and rounded growth habit. Appropriate for 10 and 12.5-cm containers. About nine weeks are requried to produce a finished 10-cm container from a rooted cutting.

*Growth and branching habit.*—Basally branching with about two lateral branches at the base.

*Plant height, base of plant to top of leaf plane.*—About 22.8 cm.

*Plant width.*—About 18 cm.

*Lateral branches.*—Length: About 11 cm. Internode length: About 1 cm. Color: 143C.

*Foliage description.*—Leaves simple, generally symmetrical, abundant, opposite. Quantity of leaves per lateral branch: About 10. Length: About 7 cm. Width: About 8 cm. Shape: Reniform with rounded apex, cordate base, and crenate margin. Texture: Downy, both surfaces pubescent. Color: Fully expanded foliage, upper surface: The inner leaf center around petiole attachment (base to center of leaf), 137B to 137C; surrounded by darker green, 137A, distinct zonation pattern (center of leaf to margin). Fully expanded foliage, lower surface: 137C. Petiole: Length: About 6.3 cm. Diameter: About 2 mm. Color: 143C.

Flower description:

*Flower type and habit.*—White and purple bi-colored flowers. Very freely and continuously flowering. Flowers arranged in spherical umbels arising from apical leaf axils. Umbels displayed above or beyond the foliage. Usually about five umbels per plant. Flowers single and round. Flowers not persistent, umbels persistent.

*Flowering season.*—Year-round under greenhouse conditions. In the garden, flowering is continuous from spring through summer.

*Umbels.*—Number of flowers per umbel: About 48. Diameter: About 10.3 cm. Height: About 7.3 cm.

*Flowers.*—Diameter: About 4.1 cm. Depth (height): About 2 cm.

*Flower buds.*—Length: About 1.7 cm. Diameter: About 7 mm. Shape: Elliptic.

*Petals.*—Quantity: Five. Length: Two upper petals: About 2.7 cm. Three lower petals: About 2.5 cm. Width: Two upper petals: About 1.9 cm. Three lower petals: About 2.2 cm. Shape: Obovate with rounded apex and entire margin. Texture: Smooth. Color: Fully opened, upper surface: Various patterns of white and purple bi-color. Typically white background with purple, 74A, and dark pink, 74D, streaks and spots. Fully opened, lower surface: Various patterns of light pink and darker pink; background light pink, 65D, 65C and 65B with small dots and streaks of darker pink, 67B.

*Peduncle* (*umbel stem*).—Length: About 18.2 cm. Strength: Strong. Angle: Mostly erect. Texture: Pubescent. Color: 143C.

*Pedicel* (*individual flower stem*).—Length: About 3.8 cm. Strength: Strong. Angle: Upright or outward. Texture: Pubescent. Color: Green, 144B, overlaid with brownish red, 184B; with subsequent development, pedicel color becomes mostly dark red, 184B.

*Reproductive organs.*—Androecium: Anther size: About 2 mm. Amount of pollen: Moderate. Pollen color: 169A. Gynoecium: Ovary color: Green.

Disease resistance: Under commercial conditions, resistance to pathogens has not been observed.

Seed development: Seed production has not been observed.

CHART A

| CHARACTERISTIC | 'BFP-1561' | 'STARBURST RED' |
|---|---|---|
| VIGOR | Moderate | Vigorous |
| PLANT HEIGHT | About 22.8 cm | About 27 cm |
| PLANT WIDTH | About 18 cm | About 18 cm |
| LATERAL BRANCH LENGTH | About 11 cm | About 12 cm |
| INTERNODE LENGTH | About 1 cm | About 2 cm |
| LEAF LENGTH | About 7 cm | About 7.5 cm |
| LEAF WIDTH | About 8 cm | About 9 cm |
| LEAF COLOR, MATURE, UPPER, SURFACE | 137B to 137C with zonation pattern, 137A | 136A with zonation pattern, 137A |
| UMBEL DIAMETER | About 10.3 cm | About 9.9 cm |
| UMBEL HEIGHT | About 7.3 cm | About 6.9 cm |
| PETAL COLOR, UPPER SURFACE | White with purple, 74A, and dark pink, 74D, streaks and spots | White with red, 47B, and light pink, 55C, streaks and spots |
| PEDUNCLE LENGTH | About 18.2 cm | About 20.3 cm |

It is claimed:

1. A new and distinct cultivar of Geranium plant named 'BFP-1561', as illustrated and described.

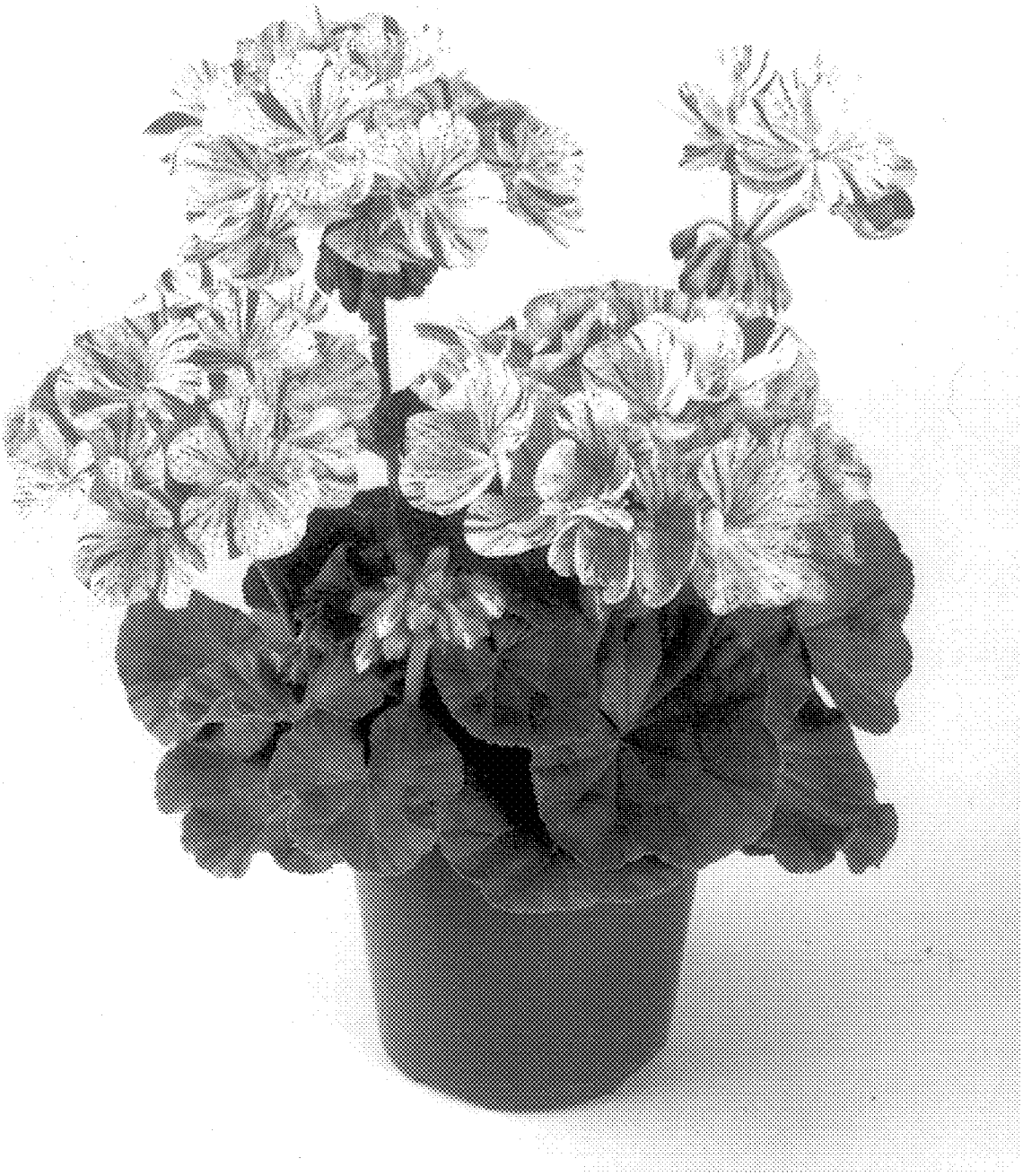

* * * * *